(12) United States Patent
Leita et al.

(10) Patent No.: US 8,710,287 B2
(45) Date of Patent: Apr. 29, 2014

(54) CINEOLE

(75) Inventors: Benjamin Aldo Leita, Rowville (AU); Peter Gray, Kew (AU); Nicholas Richard Burke, Bentleigh East (AU); Michael Shane O'Shea, Mulgrave (AU); David Lawrence Trimm, Watsons Bay (AU); Garbriella Maria Furtenbach, legal representative, Watsons Bay (AU)

(73) Assignee: Commonwealth Scientific and Industrial Research Organisation, Australian Capital Territory (AU)

( * ) Notice: Subject to any disclaimer, the term of this patent is extended or adjusted under 35 U.S.C. 154(b) by 72 days.

(21) Appl. No.: 13/383,948

(22) PCT Filed: Feb. 26, 2010

(86) PCT No.: PCT/AU2010/000232
§ 371 (c)(1), (2), (4) Date: May 22, 2012

(87) PCT Pub. No.: WO2011/006183
PCT Pub. Date: Jan. 20, 2011

(65) Prior Publication Data
US 2012/0264988 A1    Oct. 18, 2012

(30) Foreign Application Priority Data
Jul. 16, 2009    (AU) ................. 2009903333

(51) Int. Cl.
C07C 1/24    (2006.01)

(52) U.S. Cl.
USPC ......................................... 585/469; 585/357

(58) Field of Classification Search
USPC ................................ 585/469, 357
See application file for complete search history.

(56) References Cited

U.S. PATENT DOCUMENTS 2,857,439 A    10/1958    Glasebrook

FOREIGN PATENT DOCUMENTS

| DE | 195 21 222 A1 | 12/1996 |
|---|---|---|
| DE | 195 21 225 A1 | 12/1996 |
| EP | 0 282 312 | 9/1988 |
| GB | 789809 | 9/1954 |
| GB | 803747 | 9/1956 |
| JP | 63-258434 | 10/1988 |
| WO | WO 98/25873 | 6/1998 |
| WO | WO 2008/017342 A1 | 2/2008 |

OTHER PUBLICATIONS

International Search Report PCT/AU2010/000232 dated Apr. 1, 2010.
Matsuura et al., "Pyrolysis of Cineole with Activated Alumina," *Journ. of Science of the Hiroshima Univ.*, Ser. A., vol. 20, No. 3, pp. 177-186 (1957).
Hugel et al., "The Hydrogenolysis of 1,8-Cineole," *Aust. J. Chem.*, vol. 30, pp. 1287-1292 (1977).
Roberge et al., "Catalytic Aspects in the Transformation of Pinenes to p-cymene," *Applied Catalysis A: General*, vol. 215, pp. 111-124 (2001).
Buhl et al., "Production of p-cymene from α-limonene over silica supported Pd catalysts," *Applied Catalysis A; General*, vol. 188, pp. 287-299 (1999).
Grayling et al., "(R)-4-Methyl-2-Pentyl Acetate from *Eucalyptus loxophleba*," *Journ. of Natural Products*, vol. 54, No. 1, pp. 295-297 (1991).
Mizrahi et al., "Reaction gas chromatograph: II. Dehydration of monoterpene compounds on platinum-alumina catalyst," *Journ. of Chromatography A*, pp. 230-241 (1966).
Martin-Luengo et al., "Synthesis of p-cymene from limonene, a renewable feedstock," *Applied Catalysis B: Environmental*, vol. 81, pp. 218-224 (2008).
Nippon Kagaku Zasshi, vol. 81, pp. 131 to 133, dated 1960.
Notice of Reasons for Rejection dated Dec. 10, 2013 issued in connection with Japanese Application No. 2012-519847, with English translation.

*Primary Examiner* — Thuan D Dang
(74) *Attorney, Agent, or Firm* — Foley & Lardner LLP

(57) ABSTRACT

The present invention relates to a process for producing unsaturated cyclic and/or aromatic compounds from 1,8-cineole, the process comprising pyrolysing 1,8-cineole in the presence of gamma-alumina supported transition metal catalyst.

16 Claims, No Drawings

CINEOLE

FIELD OF THE INVENTION

The present invention relates in general to cineole, and in particular to a process for converting cineole into other useful compounds by pyrolysis. The invention also relates to compounds produced in accordance with the process.

BACKGROUND OF THE INVENTION

The volatility of oil prices coupled with an increasing demand for replacing petrochemical products with sustainable, bio-derived alternatives has seen a considerable amount of research effort being directed toward identifying biologically derived materials that can function as or be converted into industrially useful compounds.

1,8-cineole (hereinafter simply referred to as cineole) is a naturally occurring organic compound that may be extracted from a variety of plant species such as bay, tea tree, mugwort, sweet basil, wormwood, rosemary, sage and eucalyptus.

Cineole is the dominant component (c.a. 90 wt %) of eucalyptus oil, which is a generic collective name for oils extracted from the eucalyptus genus. The predominance of cineole in eucalyptus oil is reflected by the compounds more common name "eucalyptol".

With the volume of eucalyptus oil production increasing and its cost correspondingly decreasing, cineole presents as an attractive renewable feedstock for the production of industrially useful compounds.

An opportunity therefore remains to develop a process for converting cineole into one or more other useful compounds.

SUMMARY OF THE INVENTION

The present invention therefore provides a process for producing unsaturated cyclic and/or aromatic compounds from 1,8-cineole, the process comprising pyrolysing 1,8-cineole in the presence of gamma-alumina supported transition metal catalyst.

It has now been found that gamma-alumina supported transition metal catalysts can be used to effectively and efficiently convert cineole into one or more industrially useful unsaturated cyclic and/or aromatic compounds. In particular, the cineole may be readily converted into cyclic monoterpenoids such as p-cymene and dipentene (i.e. a racemic mixture limonene).

By adjusting the type of transition metal of the catalyst and/or the pyrolysis conditions, the process in accordance with the invention can advantageously be tailored to produce different compounds, and in particular substantially exclusive selectivity of a given compound at high yield.

In addition to producing unsaturated cyclic and/or aromatic compounds, the process in accordance with the invention can advantageously also produce hydrogen gas.

In one embodiment, the process of the invention produces unsaturated cyclic and/or aromatic monoterpenoids. In a further embodiment, the process produces dipentene and/or p-cymene.

The process in accordance with the invention can advantageously be performed using a variety of transition metals. In one embodiment, the transition metal is selected from one or more of vanadium, chromium, manganese, iron, cobalt, nickel, molybdenum, rhenium, and the precious or noble metals (i.e. ruthenium, rhodium, palladium, silver, rhenium, osmium, iridium, platinum, and gold).

Palladium has been found to be particularly effective for producing p-cymene with high conversion and selectivity.

Accordingly, in a further embodiment there is provided a process for producing p-cymene from 1,8-cineole, the process comprising pyrolysing 1,8-cineole in the presence of gamma-alumina supported palladium catalyst.

The present invention also provides for the use of gamma-alumina supported transition metal catalyst in the manufacture of unsaturated cyclic and/or aromatic compounds from 1,8-cineole.

The present invention further provides for the use of gamma-alumina supported transition metal catalyst in the pyrolysis of 1,8-cineole to manufacture unsaturated cyclic and/or aromatic compounds.

Further aspects of the invention are discussed in more detail below.

DETAILED DESCRIPTION OF THE INVENTION 1,8-Cineole is a naturally occurring organic compound having the following structure:

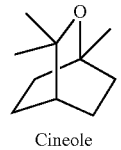

Cineole

Cineole suitable for use in accordance with the invention is readily commercially available. For example, +99% cineole may be obtained from Australian companies FGB Natural products (Felton Grimwade & Bosisto's Pty Ltd) and Kalannie Distillers. Cineole used in accordance with the invention preferably has a purity of at least 95%, more preferably at least 97%, most preferably at least 99%.

Reference to compounds produced by the process of the invention being "unsaturated" is intended to mean that such compounds comprise one or more multiple bonds. The unsaturation may form part of a cyclic and/or acyclic moiety of the compound. Generally, the unsaturation will be in the form of one or more double bonds.

The unsaturated cyclic and/or aromatic compounds produced will generally be predominantly (i.e. greater than about 50 wt. %) in the form of unsaturated cyclic and/or aromatic monoterpenoids.

The unsaturated cyclic and/or aromatic monoterpenoids will generally be C10 unsaturated cyclic and/or C10 aromatic monoterpenoids.

In one embodiment, the process produces unsaturated cyclic and/or aromatic monoterpenoids selected from dipentene and p-cymene.

Dipentene and p-cymene have the following respective structures:

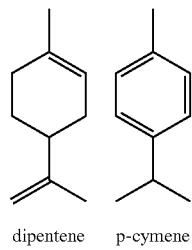

dipentene    p-cymene

In addition to the unsaturated cyclic and/or aromatic compounds (i.e. the organic or hydrophobic products), the process in accordance with the invention will generally produce water (i.e. a hydrophilic product) and optionally hydrogen, carbon monoxide and/or carbon dioxide (i.e. gaseous products). Further detail in relation to these additional products is discussed below.

The process in accordance with the invention is believed to be particularly effective at converting cineole into other industrially useful $C_{10}$ compounds. Of such compounds, p-cymene is of particular interest in that it may be used in the production of p-cresol, fragrances, pharmaceuticals, herbicides and fine chemicals.

Cymenes are conventionally derived commercially from toluene and propylene, both of which are typically derived from crude oil. The production process produces a mixture of three different isomers, with the m- and p-isomers being dominant. Further separation to pure p-cymene is generally achieved using the UOP "Cymex" process, whereby the mixture of isomers is subjected to chromatography using adsorbing (e.g. molecular sieves) and desorbing (e.g. toluene) media.

There have been investigations into the direct synthesis of p-cymene using ZSM-5 catalysts for regioselectivity in the alkylation of toluene, and also studies using pinenes as a feedstock.

However, these processes nevertheless rely on using non-renewable crude oil feedstocks.

The catalytic conversion of cineole into p-cymene is also known. However, such processes often afford relatively poor conversion and/or selectivity for p-cymene. Some processes must also be conducted at a relatively high temperature (e.g. 450° C.) so as to yield p-cymene. Such processes therefore present a number of commercial limitations.

Apart from providing flexibility for producing a number of different compounds, the process in accordance with the invention can advantageously produce p-cymene from cineole with high conversion and selectivity at relatively low temperatures. The process therefore has a number of commercial advantages over the prior art.

Unsaturated cyclic or aromatic compounds can advantageously be produced according to the process in yields of about 50 wt % or more, such as about 60 wt % or more, about 70 wt % or more, about 80 wt % or more, or even about 90 wt % or more, relative to the mass of cineole used in the process.

In one embodiment, the process of the invention produces p-cymene from cineole in an amount of about 50 wt % or more, such as about 60 wt % or more, about 70 w % or more, about 80 wt % or more, or even about 90 wt % or more, relative to the mass of cineole.

The aforementioned yields of organic compounds produced in accordance with the invention can advantageously be attained at relatively low pyrolytic temperatures. For example, one or more of the aforementioned yields may be attained by pyrolysing the cineole at temperatures ranging from about 200° C. to about 400° C., or from about 200° C. to about 350° C. In one embodiment, pyrolysis of the cineole is conducted at temperatures ranging from about 200° C. to about 275° C. The pyrolysis may be conducted at a fixed temperature, or the temperature may be varied according to a desired profile.

As used herein, the term "pyrolysing", or variants thereof such as "pyrolysis", "pyrolyse", "pyrolysed", etc, is intended to mean inducing a molecular transformation of cineole brought about by the action of heat. The molecular transformation may, for example, result from cineole undergoing dehydration and/or dehydrogenation.

Pyrolysis of cineole in accordance with the invention may be conducted using techniques well known to those skilled in the art. For example, the cineole may be conveniently pyrolysed in the vapour phase. In that case, the catalyst may be contained within a stainless steel mesh basket, which is in turn placed inside an electrically heatable tubular down-flow reactor. The reactor may then be heated to a desired temperature, for example to a temperature of about 200° C. to about 500° C.

Those skilled in the art will appreciate that a measured temperature of such a tubular reactor may not accurately reflect the temperature of the catalyst contained within the mesh basket within the reactor (which may hereinafter be referred to as the "fixed bed"). Generally, the fixed bed of catalyst will be at a lower temperature than that of the reactor tube.

For avoidance of any doubt, the temperature at which pyrolysis in accordance with the invention is to take place is that measured at the location of the catalyst, which may or may not be the measured temperature of the reactor per se. Relevant temperatures may be measured by any suitable means such as by using a thermocouple (for example a K-type thermocouple) positioned at an appropriate location.

Once the reactor has been heated to a desired temperature, cineole may be introduced. The cineole may be introduced by any suitable means, for example by way of a pump, such as a syringe pump.

Upon being introduced to the reactor the cineole may be substantially vaporised. A carrier gas may be used to assist with transporting the vaporised cineole to the fixed bed catalyst. The carrier gas may be an inert gas such as nitrogen or argon. In that case, the pyrolysis conducted in accordance with the invention may be described as an inert-pyrolysis. Alternatively, the carrier gas may comprise a reactive gas such as oxygen. In that case, the pyrolysis may be described as an oxidative-pyrolysis.

It has been found that gaseous compounds produced in accordance with the invention may vary depending upon the composition of the carrier gas. For example, where an inert carrier gas is used, primarily hydrogen can be produced. When a volume percent of oxygen is introduced into such an inert carrier gas, then the amount of hydrogen produced can decrease with a corresponding increase in oxide gas products such as carbon dioxide and/or carbon monoxide.

The presence of oxygen in the carrier gas has also been found to alter the yield and type of the unsaturated cyclic and/or aromatic compounds produced in accordance with the invention. For example, introducing a volume percent of oxygen gas into an inert carrier gas at a given temperature of the fixed bed catalyst can result in a higher conversion of cineole into the unsaturated cyclic and/or aromatic compounds.

Where a carrier gas contains a reactive gas such as oxygen, it will generally be present in an amount ranging from about 0.05 vol. % to about 22 vol. %, for example about 5 vol. % to about 15 vol. %.

In performing the process, cineole may therefore be introduced to the reactor upstream from the fixed bed catalyst, with the cineole being vaporised and transported to the fixed bed catalyst with the aid of a carrier gas.

Accordingly, in one embodiment the cineole is vaporised and a carrier gas facilitates transportation of the cineole to the catalyst.

By the cineole being pyrolysed in the "presence" of the catalyst is meant that the cineole makes contact with the catalyst at a temperature sufficient to convert the cineole into unsaturated cyclic and/or aromatic compounds.

The gamma-alumina supported transition metal catalyst used in accordance with the invention comprises gamma-alumina doped with one or more transition metals. Those skilled in the art will appreciate that gamma-alumina is a particular form of aluminium oxide that may be used as a catalytic material in its own right or, as in the present invention, a support in the production of a catalytic material.

Gamma-alumina suitable for use in catalytic applications will generally have a relatively high surface area, for example, of greater than about 10 m$^2$/g, or greater than about 50 m$^2$/g, or greater than about 100 m$^2$/g, or greater than about 200 m$^2$/g. Generally, the alumina support used in accordance with the invention will have a surface area ranging from about 10 m$^2$/g to about 240 m$^2$/g.

Gamma-alumina suitable for use in accordance with the invention can be readily obtained commercially, for example from Saint-Gobain NorPro, USA.

The gamma-alumina functions as a support for one or more transition metals, and in this form may be referred to as being "doped" with the one or more transition metals.

Provided the catalyst functions in the conversion of cineole into the unsaturated cyclic and/or aromatic compounds, there is no particular limitation on how it can be prepared. For example, the catalyst may be prepared by a wet impregnation technique. In that case, gamma-alumina, for example in the form of pellets or any other desired shape, may be doped using an aqueous solution of an appropriate metal salt (e.g. a nitrate salt) of a selected transition metal(s). The resulting doped gamma-alumina may then be dried and subsequently calcined in air to afford a catalyst material suitable for use in accordance with the invention.

In one embodiment, the catalyst is prepared by immersing a gamma-alumina support in an aqueous solution comprising transition metal salt, isolating the resulting transition metal doped gamma-alumina support from the aqueous solution, and calcining the isolated product to afford the catalyst. In such an embodiment, the concentration of the transition metal salt in the aqueous solution will generally range from about 0.1M to about 2.5M. Those skilled in the art will appreciate that some transition metal salts will form a saturated solution at concentrations less than 2.5M. In that case, the concentration range will be about 0.1M to about saturation.

In another embodiment, the catalyst is prepared by immersing a gamma-alumina support in an aqueous solution comprising transition metal salt, evaporating the aqueous liquid from the solution to isolate transition metal doped gamma-alumina support, and calcining the isolated product to afford the catalyst. In such an embodiment, the amount of transition metal used in the aqueous solution will generally be equivalent to that which is to be supported by the catalyst. In other words, due to evaporation of the aqueous liquid the gamma-alumina support can be doped with substantially all of the transition metal that was in solution.

Generally, the gamma-alumina will be doped with one or more transition metals in an amount ranging from about 0.01% to about 10%, for example from about 0.3% to about 2.5% (on a wt/wt basis of the support to transition metal(s)).

As used herein, reference to "transition metal" is intended to mean an element of the periodic table whose atom has an incomplete d sub-shell, or which can give rise to cations with an incomplete d sub-shell. Accordingly, transition metals suitable for use in accordance with the invention are intended to include those in groups 3 to 11 of the periodic table as represented in Table 1 below.

TABLE 1

Transition metals of groups 3 to 11 of the periodic table.

| Group | 3 | 4 | 5 | 6 | 7 | 8 | 9 | 10 | 11 |
|---|---|---|---|---|---|---|---|---|---|
| Period 4 | Sc 21 | Ti 22 | V 23 | Cr 24 | Mn 25 | Fe 26 | Co 27 | Ni 28 | Cu 29 |
| Period 5 | Y 39 | Zr 40 | Nb 41 | Mo 42 | Tc 43 | Ru 44 | Rh 45 | Pd 46 | Ag 47 |
| Period 6 | Lu 71 | Hf 72 | Ta 73 | W 74 | Re 75 | Os 76 | Ir 77 | Pt 78 | Au 79 |
| Period 7 | Lr 103 | Rf 104 | Db 105 | Sg 106 | Bh 107 | Hs 108 | Mt 109 | Ds 110 | Rg 111 |

In one embodiment of the invention, the transition metal is selected from one or more of those in groups 3 to 11 and periods 4 to 6 only as shown above in Table 1. In a further embodiment, the transition metal is selected from one or more of those in groups 5 to 11 and periods 4 to 6 only as shown above in Table 1. In yet a further embodiment the transition metal is selected from one or more of those in groups 5 to 10 and periods 4 to 6 only as shown above in Table 1. In a further embodiment, the transition metal is selected from one or more of vanadium, chromium, manganese, iron, cobalt, nickel, molybdenum, ruthenium, rhodium, palladium, silver, rhenium, osmium, iridium, platinum, and gold. In still a further embodiment, the transition metal is selected from one or more of ruthenium, rhodium, palladium, osmium, iridium, and platinum. In another embodiment, the transition metal is palladium, Depending upon the type of catalyst and/or pyrolysis conditions used, the nature of compounds produced in accordance with the invention can advantageously be varied.

In one embodiment, cineole is pyrolysed to produce dipentene and/or p-cymene. In that case, the catalytic transformation of cineole is believed to operate through a dehydration mechanism in the formation of dipentene and other structurally similar unsaturated cyclic monoterpenoids, and through a further dehydrogenation in the formation of p-cymene. Such a conversion mechanism is illustrated below in Scheme 1.

Scheme 1: A proposed mechanism for the conversion of cineole into unsaturated cyclic monoterpenoids via dehydration, and dehydrogenation to afford an aromatic monoterpenoid such as p-cymene.

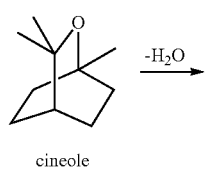

cineole

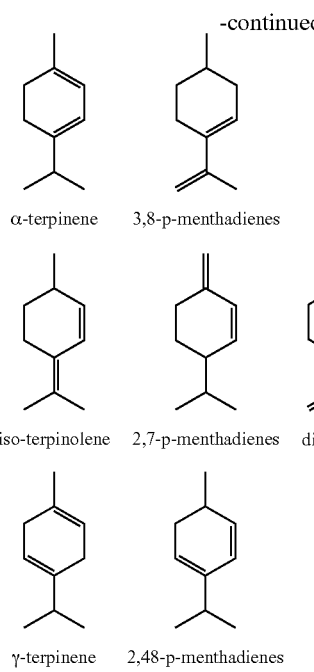

α-terpinene    3,8-p-menthadienes iso-terpinolene    2,7-p-menthadienes    dipentene    p-cymene γ-terpinene    2,48-p-menthadienes In one embodiment, the predominant organic compounds produced in accordance with the invention are dipentene and/or p-cymene. The conversion of cineole into these compounds can also afford water and gaseous products such as hydrogen, carbon monoxide and carbon dioxide. A summary of such a conversion of cineole is illustrated below in Scheme 2.

Scheme 2: Illustration of products that may be produced by pyrolysing cineole in accordance with the invention.

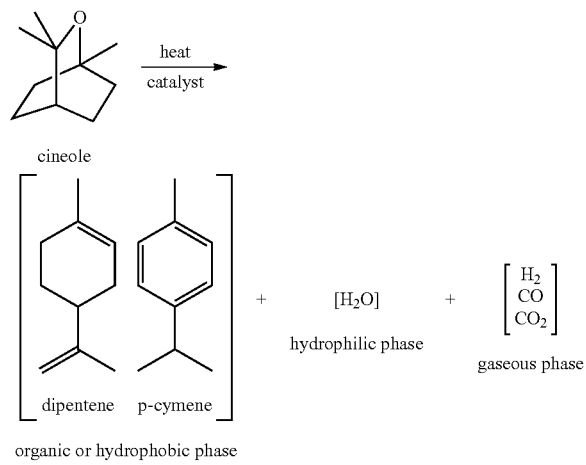

Products produced in accordance with the invention may be collected by means well known to those skilled in the art. For example, the hydrophobic and hydrophilic phases may be collected in a stainless steel trap held at an appropriate temperature. These phases will generally be condensed into a liquid upon entering the trap and can be readily separated on the basis of their immiscibility. The gaseous phase may be collected using conventional gas collection apparatus/techniques.

An advantageous feature of the present invention is that cineole may undergo a high conversion with high selectivity to a particular organic compound. Accordingly, organic compounds produced in accordance with the invention may be efficiently and effectively collected for subsequent use with minimal if no purification.

Through variation of the catalyst composition (e.g. transition metal type) and/or pyrolytic conditions employed (e.g. temperature, composition of carrier gas etc), the process in accordance with the invention can advantageously be tailored to produce specific and different products. For example, transition metals such as iron and cobalt have been found to exhibit selectivity toward producing dipentene, and transition metals such as molybdenum, chromium, palladium, manganese and ruthenium have been found to exhibit selectivity toward producing p-cymene. By varying the temperature and/or the presence of oxygen, the pyrolysis of cineole employing nickel or vanadium as the transition metal may afford p-cymene alone or a mixture of p-cymene and dipentene.

Irrespective of the transition metal employed, the yield of organic compounds produced in accordance with the invention may be adjusted by altering the temperature at which the pyrolysis is conducted and/or by altering the composition of a carrier gas. The yield of hydrogen that may be produced in accordance with the invention may also be adjusted by altering the temperature at which the pyrolysis is conducted and/or by altering the composition of a carrier gas.

The invention will hereinafter be described with reference to the following non-limiting examples.

EXAMPLES

General Experimental Details

Catalyst Preparation

High surface area gamma-alumina (hereinafter γ-$Al_2O_3$) tubular pellets having a diameter of approximately 1.5 mm (~200 $m^2g^{-1}$) were used as a slightly acidic catalyst and as a solid support for molybdenum, iron, cobalt, chromium and palladium metals. The metal-doped γ-$Al_2O_3$ catalysts were prepared by a wet impregnation technique using 1 M aqueous solutions of the appropriate metal salts.

In one procedure, 100 mL of 1 M metal nitrate solution was poured over 70 g of γ-$Al_2O_3$ pellets (Saint-Gobain NorPro, USA) that had been heated in a vacuum oven at 90° C. overnight. The mixture was stirred briefly with a spatula and left to stand at room temperature overnight. The resultant metal-impregnated γ-$Al_2O_3$ pellets were collected, washed three times with deionised water and dried in a vacuum oven at 90° C. overnight. The coated pellets were then transferred to a crucible and calcined in air at 350° C. for 12 hours. As comparative examples, undoped γ-$Al_2O_3$ pellets were subjected to the same treatment as the metal doped samples before use, and glass beads were used as a blank reaction surface.

In another procedure, γ-$Al_2O_3$ pellet support (Saint-Gobain NorPro) was first dried at 90° C. overnight in vacuo and 100 g was then immersed in palladium nitrate dihydrate (0.960 g) dissolved in distilled water (200 mL). The mixture was stirred and the solvent removed by heating to 60° C. over 4 h in vacuo. The Pd-γ-$Al_2O_3$ catalysts were then dried at 90° C. in vacuo overnight and calcined at 350° C. for 12 h. The final catalyst was found to contain 0.38% Pd on γ-$Al_2O_3$ Catalyst Regeneration The catalyst may be regenerated by first removing it from the reactor tube, placing it in a crucible, and then subjecting it to calcination in air at 350° C. for 12 h.

Stability Studies

The catalyst showed some slight deactivation over the course of an eight hour experiment prompting investigation into the long-term stability of the catalyst system. A series of four cycles of eight hour runs were conducted using the same catalytic material in each case. The first cycle used 4 g of freshly prepared 0.38% Pd-γAl$_2$O$_3$ catalyst and yielded ~92% p-cymene while showing only a slight deactivation/reduction in p-cymene yield over the eight hours, the amount of hydrogen produced by the reaction also remained constant. The reaction was stopped and a small amount of used catalyst was removed and kept for analysis by TGA. 3 g of the used catalysts was regenerated by calcination at 350° C. for 12 hours and then used in the second cycle. High yields of p-cymene (~90%) were again observed, with very similar conversion to the fresh catalysts, but the yield of p-cymene reduced over the eight hours run to ~85%. The catalyst was removed; a sample kept for TGA analysis and the rest was again subject to re calcination. The third cycle also showed high yields of p-cymene >85% initially and then a gradual reduction in catalytic activity over the eight hours to ~80%. Once again at the end of the experiment the used catalysts was removed and analysed by TGA, then re-generated by calcination. This catalyst was used for the fourth cycle, and again we observe high catalytic activity for the cineole to p-cymene conversion. On this cycle we see a slightly quicker decrease in catalytic activity finishing after the eight hours at approximately 75% yield. With the exception of the first cycle the yield of hydrogen remains relative consistent for all of the regenerated catalysts (see Tables 3 and 7).

Catalyst Characterization

Prior to surface analysis, samples were degassed under vacuum at 300° C. overnight using a VacPrep 061 Degasser. The BET surface area was determined by N$_2$ adsorption at 77 K using a Micromeretics Tristar 3000. XRD measurements were carried out using a Phillips DW 1130 machine with Cu—Kα (1.542 Å) radiation (40 kV, 25 mA) over the range 5°-80° 2□ at a scan rate of 1° min$^{-1}$ with 0.1° step size.

Catalytic Activity Measurements

All reactions were performed using a custom-designed pyrolysis rig. The vapour phase catalytic conversion of cineole was performed using an electrically heated tubular down-flow reactor (13.5 mm internal diameter, 300 mm length) with the catalyst held as a fixed bed at atmospheric pressure. A K-type thermocouple was used to monitor the temperature of the bed. Some variability in bed temperature was seen in all experiments due to cooling by feed gases. All thermocouples, furnaces, heating bands and mass flow controllers (MFC) were controlled and data was logged using specially designed software.

The liquid product was collected at 40° C. in a stainless steel trap. The gaseous products were sent through a second trap at 0° C. to an online Shimatzu GC8A Gas Chromatograph fitted with a 1 mL Valco auto sample valve.

Analysis of Liquid Products

The liquid product obtained for the majority of the samples consisted of an oily, hydrophobic phase and an aqueous phase. The analysis of the hydrophobic liquid products was performed using a Thermo Finnigan GCMS fitted with a 15M×0.1 mm ID-BPX5 0.1 μM column from Grace, using a Thermo Scientific Triplus auto sampler. For analysis, 10 μL of the hydrophobic phase was dissolved in 1.5 mL of acetonitrile (Aldrich) that had been doped with 0.1% mesitylene (Aldrich) as an internal standard. Chromatographic standards of 1,8-cineole, p-cymene and dipentene were run using the same sample preparation method. Major product p-cymene was confirmed by $^1$H and $^{13}$C NMR. Yield of p-cymene is defined as the percentage of p-cymene in the whole hydrophobic phase. Selectivity for p-cymene is defined as the percentage of p-cymene in the non-cineole fraction of the hydrophobic phase. Unless otherwise noted, the non-cineole fraction of the hydrophobic phase was comprised of the products shown in Scheme 1. The hydrophilic phase was found to be mainly water.

Analysis of Gaseous Products

The analyses of gas products were performed with an online Shimadzu GC 8A fitted with a Valco sampling valve with a 1 mL sample loop. The GC was fitted with a 12 m HAYESEP Q column and a Thermal Conductivity Detector (TCD). The GC was calibrated with the blended carrier gas as well as a calibration gas mixture containing known concentrations of hydrogen, helium, methane, nitrogen, carbon monoxide and carbon dioxide before each run. Online gas analysis was conducted at the time of collection of liquid samples.

Characterization of Catalysts, Liquid Products and Gases
Catalyst Characterization The XRD patterns of the metal doped γ-Al$_2$O$_3$ catalysts prepared by the wet impregnation technique. All the metal doped γ-Al$_2$O$_3$ samples display XRD patterns associated with the support material as well as their doped metal.

The BET surface areas for all as-prepared catalysts and γ-Al$_2$O$_3$ were measured. The surface area of the γ-Al$_2$O$_3$ was the highest while all other catalysts were lower in surface area. Metal doping of the γ-Al$_2$O$_3$ using the wet impregnation technique has shown a minimal amount of surface area loss.

Catalytic Activity

Products of the pyrolysis process were separated into three phases: hydrophobic, hydrophilic and gaseous. In all experiments, the hydrophilic layer was found to be predominantly water, while the hydrophobic phase generally contained a mixture of both aromatic and non-aromatic C$_{10}$ hydrocarbons with dipentene and p-cymene as the major products. The main gases produced were hydrogen, carbon monoxide and carbon dioxide.

Examples of Pyrolysis Runs
General Variable Temperature Experiment

In a typical variable temperature experiment, 3 g of catalyst was loaded into a stainless steel mesh basket, which was placed inside the tubular reactor. The furnace was set to an initial temperature of 250° C. and allowed to stabilise for one hour. Cineole was injected upstream of the pre-heater at a rate of 0.5 mL min-1 with an ISCO 500D syringe pump. The carrier gas was fed at a constant rate of 150 mL min-1. Once at equilibrium, gas samples were taken and liquid products collected. The furnace temperature was then raised by 50° C. and the procedure was repeated until the final reaction temperature of 500° C. was reached. Other experimental parameters are outlined blow in Table 2.

TABLE 2

Experimental parameters for variable temperature runs.

| Example | Catalysts | Amount of Oxygen in the carrier gas | Temperature range |
|---|---|---|---|
| 1 | Glass beads | 0% | 250-500° C. |
| 2 | undoped γ-Al$_2$O$_3$ pellets | 0% | 250-500° C. |
| 3 | Mo-γ-Al$_2$O$_3$ pellets | 0% | 250-500° C. |
| 4 | Cr-γ-Al$_2$O$_3$ pellets | 0% | 250-500° C. |
| 5 | Fe-γ-Al$_2$O$_3$ pellets | 0% | 250-500° C. |
| 6 | Co-γ-Al$_2$O$_3$ pellets | 0% | 250-500° C. |
| 7 | Pd-γ-Al$_2$O$_3$ pellets | 0% | 250-500° C. |
| 8 | Ni-γ-Al$_2$O$_3$ pellets | 0% | 250-500° C. |
| 9 | Ru-γ-Al$_2$O$_3$ pellets | 0% | 250-500° C. |
| 10 | Glass beads | 7.3% | 250-500° C. |

TABLE 2-continued

Experimental parameters for variable temperature runs.

| Example | Catalysts | Amount of Oxygen in the carrier gas | Temperature range |
|---|---|---|---|
| 11 | undoped γ-Al$_2$O$_3$ pellets | 7.3% | 250-500° C. |
| 12 | Mo-γ-Al$_2$O$_3$ pellets | 7.3% | 250-500° C. |
| 13 | Cr-γ-Al$_2$O$_3$ pellets | 7.3% | 250-500° C. |
| 14 | Fe-γ-Al$_2$O$_3$ pellets | 7.3% | 250-500° C. |
| 15 | Co-γ-Al$_2$O$_3$ pellets | 7.3% | 250-500° C. |
| 16 | Pd-γ-Al$_2$O$_3$ pellets | 7.3% | 250-500° C. |
| 17 | Mn-γ-Al$_2$O$_3$ pellets | 7.3% | 250-500° C. |
| 18 | V-γ-Al$_2$O$_3$ pellets | 7.3% | 250-500° C. |
| 19 | Ni-γ-Al$_2$O$_3$ pellets | 7.3% | 250-500° C. |
| 20 | Ru-γ-Al$_2$O$_3$ pellets | 7.3% | 250-500° C. |
| 21 | Glass beads | 14.6% | 250-500° C. |
| 22 | undoped γ-Al$_2$O$_3$ pellets | 14.6% | 250-500° C. |
| 23 | Mo-γ-Al$_2$O$_3$ pellets | 14.6% | 250-500° C. |
| 24 | Cr-γ-Al$_2$O$_3$ pellets | 14.6% | 250-500° C. |
| 25 | Fe-γ-Al$_2$O$_3$ pellets | 14.6% | 250-500° C. |
| 26 | Co-γ-Al$_2$O$_3$ pellets | 14.6% | 250-500° C. |
| 27 | Pd-γ-Al$_2$O$_3$ pellets | 14.6% | 250-500° C. |
| 28 | Ni-γ-Al$_2$O$_3$ pellets | 14.6% | 250-500° C. |
| 29 | Ru-γ-Al$_2$O$_3$ pellets | 14.6% | 250-500° C. |

General Fixed Bed Temperature Experiment

In a typical fixed bed temperature experiment, 4 g of catalyst was loaded into a stainless steel mesh basket, which was placed inside the tubular reactor. The furnace was set so that the bed temperature was the required temperature and allowed to stabilise for one hour. Cineole was injected upstream of the pre-heater at a rate of 0.3 mL min$^{-1}$ with an ISCO 500D syringe pump. The carrier gas was fed at a constant rate of 150 mL min$^{-1}$. Once at equilibrium, gas samples were taken and liquid products collected. Other experimental parameters are outlined blow in Table 3.

TABLE 3

Experimental parameters for fixed temperature runs.

| Example | Catalysts | Amount of Oxygen in the feed gas | Length of experiment (Min) | Temperature |
|---|---|---|---|---|
| 30 | Pd-γ-Al$_2$O$_3$ pellets | 7.3% | 90 | 200° C. |
| 31 | Pd-γ-Al$_2$O$_3$ pellets | 7.3% | 180 | 220° C. |
| 32 | Pd-γ-Al$_2$O$_3$ pellets | 7.3% | 180 | 240° C. |
| 33 | Pd-γ-Al$_2$O$_3$ pellets | 7.3% | 180 | 260° C. |
| 34 | Pd-γ-Al$_2$O$_3$ pellets | 7.3% | 180 | 280° C. |
| 35 | Pd-γ-Al$_2$O$_3$ pellets | 7.3% | 180 | 300° C. |
| 36 | Pd-γ-Al$_2$O$_3$ pellets | 0% | 180 | 250° C. |
| 37 | Pd-γ-Al$_2$O$_3$ pellets | 7.3% | 180 | 250° C. |
| 38 | Pd-γ-Al$_2$O$_3$ pellets | 14.6% | 180 | 250° C. |
| 39 | Pd-γ-Al$_2$O$_3$ pellets 1$^{st}$ regen cycle | 7.3% | 480 | 250° C. |
| 40 | Pd-γ-Al$_2$O$_3$ pellets 2$^{nd}$ regen cycle | 7.3% | 480 | 250° C. |
| 41 | Pd-γ-Al$_2$O$_3$ pellets 3$^{rd}$ regen cycle | 7.3% | 480 | 250° C. |
| 42 | Pd-γ-Al$_2$O$_3$ pellets 4$^{th}$ regen cycle | 7.3% | 480 | 250° C. |

For examples 36-42 a new batch of Pd-γ-Al$_2$O$_3$ pellets was made with a slightly modified procedure. In a typical procedure, a given amount of metal nitrate salt was dissolved in water and poured over the γ-Al$_2$O$_3$ pellets (Saint-Gobain Nor-Pro, USA) that had been heated in a vacuum oven at 90° C. overnight. The mixture was stirred on a rotary evaporator for 3 hours and then the water removed by vacuum. The resultant metal-impregnated γ-Al$_2$O$_3$ pellets were collected, and dried in a vacuum oven at 90° C. overnight. The coated pellets were then transferred to a crucible and calcined in air at 350° C. for 12 hours.

Hydrophobic Phase Analysis

Cineole remained relatively unchanged for all experiments using the glass beads.

Analysis data for the remaining samples is presented below in Tables 4-7.

TABLE 4

Major products in the hydrophobic phase from the conversion of cineole with no oxygen in the feed gas. Variable temperature runs.

| Example | Catalyst | Furnace Temp (° C.) | Bed Temp (° C.) | p-cymene (%) | Dipentene (%) | Cineole (%) |
|---|---|---|---|---|---|---|
| 2 | γ-Al$_2$O$_3$ | 250 | 214 | 6 | 0 | 93 |
|   |   | 300 | 212 | 23 | 0 | 76 |
|   |   | 350 | 262 | 31 | 0 | 65 |
|   |   | 400 | 285 | 47 | 0 | 35 |
|   |   | 450 | 357 | 39 | 0 | 20 |
|   |   | 500 | 406 | 26 | 0 | 6 |
| 3 | Mo-γ-Al$_2$O$_3$ | 250 | 199 | 9 | 0 | 51 |
|   |   | 300 | 184 | 16 | 0 | 51 |
|   |   | 350 | 207 | 14 | 0 | 48 |
|   |   | 400 | 274 | 8 | 0 | 34 |
|   |   | 450 | 335 | 33 | 0 | 24 |
|   |   | 500 | 378 | 56 | 0 | 15 |
| 4 | Cr-γ-Al$_2$O$_3$ | 250 | 205 | 11 | 0 | 88 |
|   |   | 300 | 220 | 18 | 0 | 81 |
|   |   | 350 | 250 | 2 | 0 | 83 |
|   |   | 400 | 293 | 18 | 0 | 40 |
|   |   | 450 | 344 | 23 | 0 | 24 |
|   |   | 500 | 394 | 35 | 0 | 13 |
| 5 | Fe-γ-Al$_2$O$_3$ | 250 | 224 | 0 | 12 | 87 |
|   |   | 300 | 228 | 0 | 23 | 76 |
|   |   | 350 | 250 | 0 | 56 | 42 |
|   |   | 400 | 279 | 0 | 76 | 15 |
|   |   | 450 | 325 | 0 | 64 | 4 |
|   |   | 500 | 379 | 0 | 0 | 40 |
| 6 | Co-γ-Al$_2$O$_3$ | 250 | 209 | 0 | 0 | 100 |
|   |   | 300 | 229 | 0 | 55 | 42 |

TABLE 4-continued

Major products in the hydrophobic phase from the conversion of cineole
with no oxygen in the feed gas. Variable temperature runs.

| Example | Catalyst | Furnace Temp (° C.) | Bed Temp (° C.) | p-cymene (%) | Dipentene (%) | Cineole (%) |
|---|---|---|---|---|---|---|
| | | 350 | 267 | 0 | 66 | 26 |
| | | 400 | 315 | 0 | 71 | 15 |
| | | 450 | 361 | 0 | 64 | 8 |
| | | 500 | 411 | 0 | 57 | 7 |
| 7 | Pd-γ-Al$_2$O$_3$ | 250 | 214 | 57 | 0 | 37 |
| | | 300 | 231 | 56 | 0 | 42 |
| | | 350 | 269 | 67 | 0 | 29 |
| | | 400 | 305 | 77 | 0 | 18 |
| | | 450 | 347 | 85 | 0 | 11 |
| | | 500 | 385 | 88 | 0 | 6 |
| 8 | Ni-γ-Al$_2$O$_3$ | 250 | 208 | 32 | 0 | 67 |
| | | 300 | 211 | 39 | 0 | 60 |
| | | 350 | 243 | 58 | 0 | 36 |
| | | 400 | 292 | 66 | 0 | 21 |
| | | 450 | 337 | 53 | 17 | 10 |
| | | 500 | 379 | 28 | 52 | 5 |
| 9 | Ru-γ-Al$_2$O$_3$ | 250 | 208 | 44 | 0 | 33 |
| | | 300 | 213 | 40 | 0 | 18 |
| | | 350 | 256 | 29 | 0 | 8 |
| | | 400 | 316 | 22 | 0 | 3 |
| | | 450 | 379 | 27 | 0 | 2 |
| | | 500 | 430 | 34 | 0 | 1 |

TABLE 5

Major products in the hydrophobic phase from the conversion of cineole
with 7.3% oxygen in the feed gas. Variable temperature runs.

| Example | Catalyst | Furnace Temp (° C.) | Bed Temp (° C.) | p-cymene (%) | Dipentene (%) | Cineole (%) |
|---|---|---|---|---|---|---|
| 11 | γ-Al$_2$O$_3$ | 250 | 199 | 0 | 0 | 95 |
| | | 300 | 210 | 46 | 0 | 45 |
| | | 350 | 248 | 49 | 0 | 46 |
| | | 400 | 283 | 58 | 0 | 34 |
| | | 450 | 343 | 60 | 0 | 21 |
| | | 500 | 393 | 50 | 0 | 10 |
| 12 | Mo-γ-Al$_2$O$_3$ | 250 | 205 | 9 | 0 | 52 |
| | | 300 | 250 | 54 | 0 | 18 |
| | | 350 | 279 | 52 | 0 | 17 |
| | | 400 | 318 | 52 | 0 | 18 |
| | | 450 | 356 | 54 | 0 | 22 |
| | | 500 | 393 | 56 | 0 | 25 |
| 13 | Cr-γ-Al$_2$O$_3$ | 250 | 200 | 23 | 0 | 42 |
| | | 300 | 225 | 9 | 0 | 91 |
| | | 350 | 265 | 14 | 0 | 85 |
| | | 400 | 307 | 25 | 0 | 71 |
| | | 450 | 349 | 39 | 0 | 45 |
| | | 500 | 392 | 47 | 0 | 33 |
| 14 | Fe-γ-Al$_2$O$_3$ | 250 | 227 | 0 | 61 | 19 |
| | | 300 | 249 | 0 | 41 | 53 |
| | | 350 | 282 | 0 | 42 | 54 |
| | | 400 | 321 | 0 | 45 | 46 |
| | | 450 | 363 | 0 | 48 | 40 |
| | | 500 | 408 | 0 | 53 | 35 |
| 15 | Co-γ-Al$_2$O$_3$ | 250 | 233 | 0 | 3 | 97 |
| | | 300 | 252 | 0 | 4 | 96 |
| | | 350 | 289 | 0 | 10 | 90 |
| | | 400 | 323 | 0 | 26 | 71 |
| | | 450 | 365 | 0 | 44 | 48 |
| | | 500 | 419 | 0 | 55 | 23 |
| 16 | Pd-γ-Al$_2$O$_3$ | 250 | 234 | 89 | 0 | 10 |
| | | 300 | 252 | 91 | 0 | 8 |
| | | 350 | 293 | 95 | 0 | 5 |
| | | 400 | 328 | 94 | 0 | 3 |
| | | 450 | 374 | 68 | 0 | 1 |
| | | 500 | 425 | 50 | 0 | 2 |
| 17 | Mn-γ-Al$_2$O$_3$ | 250 | 213 | 0 | 0 | 91 |
| | | 300 | 215 | 36 | 0 | 45 |
| | | 350 | 251 | 38 | 0 | 42 |
| | | 400 | 290 | 50 | 0 | 34 |

TABLE 5-continued

Major products in the hydrophobic phase from the conversion of cineole with 7.3% oxygen in the feed gas. Variable temperature runs.

| Example | Catalyst | Furnace Temp (° C.) | Bed Temp (° C.) | p-cymene (%) | Dipentene (%) | Cineole (%) |
|---|---|---|---|---|---|---|
| | | 450 | 339 | 52 | 0 | 21 |
| | | 500 | 406 | 48 | 0 | 10 |
| 18 | V-γ-Al$_2$O$_3$ | 250 | 229 | 10 | 0 | 65 |
| | | 300 | 232 | 52 | 0 | 4 |
| | | 350 | 275 | 51 | 3 | 3 |
| | | 400 | 340 | 49 | 2 | 3 |
| | | 450 | 401 | 46 | 2 | 5 |
| | | 500 | 445 | 46 | 1 | 9 |
| 19 | Ni-γ-Al$_2$O$_3$ | 250 | 198 | 27 | 0 | 72 |
| | | 300 | 202 | 24 | 0 | 75 |
| | | 350 | 232 | 45 | 0 | 53 |
| | | 400 | 281 | 57 | 0 | 36 |
| | | 450 | 332 | 58 | 0 | 34 |
| | | 500 | 377 | 59 | 0 | 29 |
| 20 | Ru-γ-Al$_2$O$_3$ | 250 | 208 | 42 | 0 | 50 |
| | | 300 | 213 | 45 | 0 | 42 |
| | | 350 | 256 | 51 | 0 | 29 |
| | | 400 | 316 | 51 | 0 | 18 |
| | | 450 | 379 | 36 | 0 | 7 |
| | | 500 | 430 | 41 | 0 | 4 |

TABLE 6

Major products in the hydrophobic phase from the conversion of cineole with 14.6% oxygen in the feed gas. Variable temperature runs.

| Example | Catalyst | Furnace Temp (° C.) | Bed Temp (° C.) | p-cymene (%) | Dipentene (%) | Cineole (%) |
|---|---|---|---|---|---|---|
| 22 | γ-Al$_2$O$_3$ | 250 | 195 | 6 | 0 | 94 |
| | | 300 | 216 | 18 | 0 | 78 |
| | | 350 | 252 | 42 | 0 | 54 |
| | | 400 | 312 | 51 | 0 | 41 |
| | | 450 | 360 | 51 | 0 | 34 |
| | | 500 | 397 | 47 | 0 | 24 |
| 23 | Mo-γ-Al$_2$O$_3$ | 250 | 228 | 32 | 0 | 19 |
| | | 300 | 266 | 52 | 0 | 25 |
| | | 350 | 292 | 41 | 0 | 41 |
| | | 400 | 325 | 38 | 0 | 48 |
| | | 450 | 358 | 34 | 0 | 53 |
| | | 500 | 393 | 38 | 0 | 50 |
| 24 | Cr-γ-Al$_2$O$_3$ | 250 | 224 | 14 | 0 | 83 |
| | | 300 | 248 | 11 | 0 | 89 |
| | | 350 | 302 | 23 | 0 | 73 |
| | | 400 | 346 | 36 | 0 | 49 |
| | | 450 | 387 | 46 | 0 | 30 |
| | | 500 | 427 | 55 | 0 | 17 |
| 25 | Fe-γ-Al$_2$O$_3$ | 250 | 224 | 0 | 4 | 95 |
| | | 300 | 261 | 0 | 50 | 42 |
| | | 350 | 286 | 0 | 48 | 44 |
| | | 400 | 318 | 0 | 51 | 37 |
| | | 450 | 363 | 0 | 52 | 32 |
| | | 500 | 406 | 0 | 58 | 25 |
| 26 | Co-γ-Al$_2$O$_3$ | 250 | 228 | 0 | 34 | 63 |
| | | 300 | 248 | 0 | 26 | 74 |
| | | 350 | 297 | 0 | 26 | 74 |
| | | 400 | 344 | 0 | 33 | 63 |
| | | 450 | 411 | 0 | 47 | 45 |
| | | 500 | 459 | 0 | 58 | 22 |
| 27 | Pd-γ-Al$_2$O$_3$ | 250 | 293 | 93 | 0 | 5 |
| | | 300 | 301 | 94 | 0 | 5 |
| | | 350 | 317 | 89 | 0 | 5 |
| | | 400 | 350 | 81 | 0 | 4 |
| | | 450 | 393 | 50 | 0 | 2 |
| | | 500 | 440 | 52 | 0 | 1 |
| 28 | Ni-γ-Al$_2$O$_3$ | 250 | 198 | 18 | 0 | 78 |
| | | 300 | 206 | 32 | 0 | 67 |
| | | 350 | 243 | 37 | 0 | 62 |
| | | 400 | 292 | 45 | 0 | 54 |
| | | 450 | 342 | 44 | 9 | 30 |
| | | 500 | 384 | 37 | 29 | 13 |

TABLE 6-continued

Major products in the hydrophobic phase from the conversion of cineole with 14.6% oxygen in the feed gas. Variable temperature runs.

| Example | Catalyst | Furnace Temp (° C.) | Bed Temp (° C.) | p-cymene (%) | Dipentene (%) | Cineole (%) |
|---|---|---|---|---|---|---|
| 29 | Ru-γ-Al$_2$O$_3$ | 250 | 214 | 47 | 0 | 38 |
|  |  | 300 | 225 | 46 | 0 | 41 |
|  |  | 350 | 269 | 49 | 0 | 35 |
|  |  | 400 | 335 | 51 | 0 | 26 |
|  |  | 450 | 406 | 50 | 0 | 17 |
|  |  | 500 | 436 | 46 | 0 | 8 |

TABLE 7

Fixed temperature runs, yields of p-cymene.

| Example | Catalysts | Amount of Oxygen in the feed gas | Yield of p-cymene (%) average yield | Temperature range |
|---|---|---|---|---|
| 30 | Pd-γ-Al$_2$O$_3$ pellets | 7.3% | 25 | 200° C. |
| 31 | Pd-γ-Al$_2$O$_3$ pellets | 7.3% | 27 | 220° C. |
| 32 | Pd-γ-Al$_2$O$_3$ pellets | 7.3% | 79 | 240° C. |
| 33 | Pd-γ-Al$_2$O$_3$ pellets | 7.3% | 70 | 260° C. |
| 34 | Pd-γ-Al$_2$O$_3$ pellets | 7.3% | 65 | 280° C. |
| 35 | Pd-γ-Al$_2$O$_3$ pellets | 7.3% | 60 | 300° C. |
| 36 | Pd-γ-Al$_2$O$_3$ pellets | 0% | 99.1 | 250° C. |
| 37 | Pd-γ-Al$_2$O$_3$ pellets | 7.3% | 98.6 | 250° C. |
| 38 | Pd-γ-Al$_2$O$_3$ pellets | 14.6% | 99.5 | 250° C. |
| 39 | Pd-γ-Al$_2$O$_3$ pellets 1$^{st}$ regen cycle | 7.3% | 91 | 250° C. |
| 40 | Pd-γ-Al$_2$O$_3$ pellets 2$^{nd}$ regen cycle | 7.3% | 89 | 250° C. |
| 41 | Pd-γ-Al$_2$O$_3$ pellets 3$^{rd}$ regen cycle | 7.3% | 84 | 250° C. |
| 42 | Pd-γ-Al$_2$O$_3$ pellets 4$^{th}$ regen cycle | 7.3% | 77 | 250° C. |

Gas Analysis

Analysis data for each sample is presented below in Tables 8-10.

TABLE 8

Gas analysis with no oxygen in feed gas

| Example | Catalyst | Furnace Temp (° C.) | Bed Temp (° C.) | Hydrogen (% in exit gas) | Carbon monoxide (% in exit gas) | Carbon dioxide (% in exit gas) |
|---|---|---|---|---|---|---|
| 1 | Glass beads | 250 | 226 | 0 | 0 | 0 |
|  |  | 300 | 236 | 0 | 0 | 0 |
|  |  | 350 | 279 | 0 | 0 | 0 |
|  |  | 400 | 328 | 0 | 0 | 0 |
|  |  | 450 | 373 | 0 | 0 | 0 |
|  |  | 500 | 419 | 0 | 0 | 0 |
| 2 | γ-Al$_2$O$_3$ | 250 | 214 | 0 | 0 | 0 |
|  |  | 300 | 212 | 0 | 0 | 0 |
|  |  | 350 | 262 | 0 | 0 | 0 |
|  |  | 400 | 285 | 0 | 0 | 0 |
|  |  | 450 | 357 | 0 | 0 | 0 |
|  |  | 500 | 406 | 0.8 | 0 | 0 |
| 3 | Mo-γ-Al$_2$O$_3$ | 250 | 199 | 0 | 0 | 0 |
|  |  | 300 | 184 | 0 | 0 | 0 |
|  |  | 350 | 207 | 0 | 0 | 0 |
|  |  | 400 | 274 | 0 | 0 | 0 |
|  |  | 450 | 335 | 2.5 | 2.9 | 0 |
|  |  | 500 | 378 | 9.2 | 3 | 0 |
| 4 | Cr-γ-Al$_2$O$_3$ | 250 | 205 | 0 | 0 | 0 |
|  |  | 300 | 220 | 0 | 0 | 0 |
|  |  | 350 | 250 | 0 | 0 | 0 |
|  |  | 400 | 293 | 0.1 | 0 | 0 |
|  |  | 450 | 344 | 4.7 | 0 | 0 |
|  |  | 500 | 394 | 12.3 | 0 | 0 |
| 5 | Co-γ-Al$_2$O$_3$ | 250 | 224 | 0 | 0 | 0 |
|  |  | 300 | 228 | 0 | 0 | 0 |
|  |  | 350 | 250 | 0 | 0 | 0 |
|  |  | 400 | 279 | 0 | 0 | 0 |
|  |  | 450 | 325 | 0 | 0 | 0 |
|  |  | 500 | 379 | 6.3 | 1.7 | 0 |
| 6 | Fe-γ-Al$_2$O$_3$ | 250 | 209 | 0 | 0 | 0 |
|  |  | 300 | 229 | 0 | 0 | 0 |
|  |  | 350 | 267 | 0 | 0 | 0 |
|  |  | 400 | 315 | 0 | 0 | 0 |

TABLE 8-continued

Gas analysis with no oxygen in feed gas

| Example | Catalyst | Furnace Temp (° C.) | Bed Temp (° C.) | Hydrogen (% in exit gas) | Carbon monoxide (% in exit gas) | Carbon dioxide (% in exit gas) |
|---|---|---|---|---|---|---|
| | | 450 | 361 | 0.2 | 0 | 0 |
| | | 500 | 411 | 4.6 | 0 | 0 |
| 7 | Pd-γ-$Al_2O_3$ | 250 | 214 | 17.8 | 0 | 0 |
| | | 300 | 231 | 21.7 | 0 | 0 |
| | | 350 | 269 | 28.2 | 0 | 0 |
| | | 400 | 305 | 37.6 | 0 | 0 |
| | | 450 | 347 | 39.7 | 0 | 0 |
| | | 500 | 385 | 40.1 | 0 | 0 |

TABLE 9

Gas analysis with 7.3% oxygen in feed gas

| Example | Catalyst | Furnace Temp (° C.) | Bed Temp (° C.) | Hydrogen (% in exit gas) | Carbon monoxide (% in exit gas) | Carbon dioxide (% in exit gas) |
|---|---|---|---|---|---|---|
| 10 | Glass beads | 250 | 232 | 0 | 0 | 0 |
| | | 300 | 245 | 0 | 0 | 0 |
| | | 350 | 283 | 0 | 0 | 0 |
| | | 400 | 334 | 0 | 0 | 0 |
| | | 450 | 383 | 0 | 0 | 0 |
| | | 500 | 432 | 0 | 0 | 0 |
| 11 | γ-$Al_2O_3$ | 250 | 199 | 0 | 0 | 0 |
| | | 300 | 210 | 0 | 0 | 0 |
| | | 350 | 248 | 0 | 0 | 0 |
| | | 400 | 283 | 0 | 0 | 0.2 |
| | | 450 | 343 | 0 | 0 | 0.6 |
| | | 500 | 393 | 1.3 | 0 | 0.9 |
| 12 | Mo-γ-$Al_2O_3$ | 250 | 205 | 0 | 0 | 0 |
| | | 300 | 250 | 0 | 0 | 0 |
| | | 350 | 279 | 0 | 0 | 0.1 |
| | | 400 | 318 | 0.8 | 0 | 0.3 |
| | | 450 | 356 | 3.6 | 0.1 | 1.2 |
| | | 500 | 393 | 7.8 | 0.2 | 1.7 |
| 13 | Cr-γ-$Al_2O_3$ | 250 | 200 | 0 | 0 | 0 |
| | | 300 | 225 | 0 | 0 | 0 |
| | | 350 | 265 | 0 | 0 | 2.0 |
| | | 400 | 307 | 0 | 0 | 3.3 |
| | | 450 | 349 | 0 | 0 | 4.1 |
| | | 500 | 392 | 1.0 | 0.8 | 4.0 |
| 14 | Fe-γ-$Al_2O_3$ | 250 | 227 | 0 | 0 | 0 |
| | | 300 | 249 | 0 | 0 | 0 |
| | | 350 | 282 | 0 | 0 | 2.6 |
| | | 400 | 321 | 0 | 0 | 3.6 |
| | | 450 | 363 | 0 | 0 | 5.9 |
| | | 500 | 408 | 1.6 | 0.1 | 9.6 |
| 15 | Co-γ-$Al_2O_3$ | 250 | 233 | 0 | 0 | 0 |
| | | 300 | 252 | 0 | 0 | 0 |
| | | 350 | 289 | 0 | 0 | 1.3 |
| | | 400 | 323 | 0 | 0 | 2.2 |
| | | 450 | 365 | 0 | 0.1 | 8.0 |
| | | 500 | 419 | 0.2 | 0.2 | 11.0 |
| 16 | Pd-γ-$Al_2O_3$ | 250 | 234 | 21.7 | 0 | 0.6 |
| | | 300 | 252 | 27.7 | 0 | 0.9 |
| | | 350 | 293 | 30.5 | 0 | 1.5 |
| | | 400 | 328 | 30.4 | 0 | 3.2 |
| | | 450 | 374 | 23.2 | 0 | 5.8 |
| | | 500 | 425 | 15.7 | 0 | 10.4 |

TABLE 10

Gas analysis with 7.3% oxygen in feed gas

| Example | Catalyst | Furnace Temp (° C.) | Bed Temp (° C.) | Hydrogen (% in exit gas) | Carbon monoxide (% in exit gas) | Carbon dioxide (% in exit gas) |
|---|---|---|---|---|---|---|
| 21 | Glass beads | 250 | 249 | 0 | 0 | 0 |
| | | 300 | 251 | 0 | 0 | 0 |

TABLE 10-continued

Gas analysis with 7.3% oxygen in feed gas

| Example | Catalyst | Furnace Temp (° C.) | Bed Temp (° C.) | Hydrogen (% in exit gas) | Carbon monoxide (% in exit gas) | Carbon dioxide (% in exit gas) |
|---|---|---|---|---|---|---|
| | | 350 | 288 | 0 | 0 | 0 |
| | | 400 | 333 | 0 | 0 | 0 |
| | | 450 | 384 | 0 | 0 | 0 |
| | | 500 | 438 | 0 | 0 | 0 |
| 22 | γ-Al$_2$O$_3$ | 250 | 195 | 0 | 0 | 0 |
| | | 300 | 216 | 0 | 0 | 0 |
| | | 350 | 252 | 0 | 0 | 0 |
| | | 400 | 312 | 0 | 0 | 0.7 |
| | | 450 | 360 | 0 | 0 | 1.4 |
| | | 500 | 397 | 0.2 | 0.1 | 1.6 |
| 23 | Mo-γ-Al$_2$O$_3$ | 250 | 228 | 0 | 0 | 0 |
| | | 300 | 266 | 0 | 0 | 1.0 |
| | | 350 | 292 | 0 | 0 | 2.1 |
| | | 400 | 325 | 0.5 | 0 | 4.5 |
| | | 450 | 358 | 2.1 | 0.1 | 6.9 |
| | | 500 | 393 | 5.9 | 0.2 | 4.0 |
| 24 | Cr-γ-Al$_2$O$_3$ | 250 | 224 | 0 | 0 | 0 |
| | | 300 | 248 | 0 | 0 | 1.0 |
| | | 350 | 302 | 0 | 0.1 | 3.4 |
| | | 400 | 346 | 0.1 | 0.1 | 6.4 |
| | | 450 | 387 | 0.9 | 0.2 | 6.4 |
| | | 500 | 427 | 5.0 | 0.4 | 6.8 |
| 25 | Fe-γ-Al$_2$O$_3$ | 250 | 224 | 0 | 0 | 0 |
| | | 300 | 261 | 0 | 0 | 0 |
| | | 350 | 286 | 0 | 0 | 4.5 |
| | | 400 | 318 | 0 | 0.1 | 5.6 |
| | | 450 | 363 | 0.6 | 0.1 | 7.9 |
| | | 500 | 406 | 2.5 | 0.3 | 10.1 |
| 26 | Co-γ-Al$_2$O$_3$ | 250 | 228 | 0 | 0 | 0 |
| | | 300 | 248 | 0 | 0 | 0 |
| | | 350 | 297 | 0.1 | 0 | 0 |
| | | 400 | 344 | 0.1 | 0.1 | 5.3 |
| | | 450 | 411 | 0.6 | 0.2 | 7.8 |
| | | 500 | 459 | 1.5 | 0.3 | 13.5 |
| 27 | Pd-γ-Al$_2$O$_3$ | 250 | 293 | 21.6 | 0 | 4.3 |
| | | 300 | 301 | 27.5 | 0 | 5.4 |
| | | 350 | 317 | 28.6 | 0 | 7.4 |
| | | 400 | 350 | 25.2 | 0.1 | 9.8 |
| | | 450 | 393 | 18.7 | 0 | 10.6 |
| | | 500 | 440 | 13.0 | 0.1 | 10.2 |

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The invention claimed is:

1. A process for producing unsaturated cyclic and/or aromatic compounds from 1,8-cineole, the process comprising pyrolysing 1,8-cineole in the presence of gamma-alumina supported transition metal catalyst thereby to produce the unsaturated cyclic and/or aromatic compounds.

2. The process according to claim 1, wherein the unsaturated cyclic and/or aromatic compounds are monoterpenoids.

3. The process according to claim 1, wherein the unsaturated cyclic and/or aromatic compounds are C10 monoterpenoids.

4. The process according to claim 1, wherein the unsaturated cyclic and/or aromatic compounds are selected from dipentene and p-cymene.

5. The process according to claim 1, wherein the transition metal is selected from one or more of vanadium, chromium, manganese, iron, cobalt, nickel, molybdenum, rhenium, ruthenium, rhodium, palladium, silver, rhenium, osmium, iridium, platinum, and gold.

6. The process according to claim 5, wherein the transition metal is selected from ruthenium, rhodium, palladium, osmium, iridium and platinum.

7. The process according to claim 1, wherein the unsaturated cyclic and/or aromatic compounds are produced in an amount of at least 70 wt %, relative to the amount of 1,8-cineole used.

8. The process according to claim 7, wherein the unsaturated cyclic and/or aromatic compounds are produced in an amount of at least 80 wt %, relative to the amount of 1,8-cineole used.

9. The process according to claim 1, wherein the pyrolysis is conducted at a temperature ranging from about 200° C. to about 350° C.

10. The process according to claim 1, wherein the pyrolysis comprises contacting the gamma-alumina supported transition metal catalyst with vaporised 1,8-cineole.

11. The process according to claim 10, wherein the vaporised 1,8-cineole comprises a carrier gas selected from nitrogen, argon and oxygen.

12. The process according to claim 11, wherein the carrier gas is oxygen.

13. The process according to claim 1, wherein the gamma-alumina supported transition metal catalyst is prepared by immersing a gamma-alumina support in an aqueous solution comprising transition metal salt, isolating the resulting transition metal doped gamma-alumina support from the aqueous solution, and calcining the isolated product to afford the catalyst.

14. The process according to claim 1, wherein the gamma-alumina supported transition metal catalyst is prepared by immersing a gamma-alumina support in an aqueous solution comprising transition metal salt, evaporating the aqueous liquid from the solution to isolate transition metal doped gamma-alumina support, and calcining the isolated product to afford the catalyst.

15. The process according to claim 13, wherein the gamma-alumina support has a surface area of greater than about 10 m2/g.

16. The process according to claim 1, wherein the gamma-alumina supported transition metal catalyst comprises from about 0.01% to about 10% of one or more transition metals on a wt/wt basis of the gamma-alumina support to transition metal(s).

* * * * *